US010056868B2

(12) United States Patent
Deliwala et al.

(10) Patent No.: US 10,056,868 B2
(45) Date of Patent: Aug. 21, 2018

(54) FOUR-STAGE CIRCUIT ARCHITECTURE FOR DETECTING PULSED SIGNALS

(71) Applicant: ANALOG DEVICES, INC., Norwood, MA (US)

(72) Inventors: Shrenik Deliwala, Andover, MA (US); Steven J. Decker, Sandown, MA (US); Dan M. Weinberg, Westford, MA (US)

(73) Assignee: ANALOG DEVICES, INC., Norwood, MA (US)

( * ) Notice: Subject to any disclaimer, the term of this patent is extended or adjusted under 35 U.S.C. 154(b) by 227 days.

(21) Appl. No.: 14/808,083

(22) Filed: Jul. 24, 2015

(65) Prior Publication Data

US 2015/0333712 A1 Nov. 19, 2015

Related U.S. Application Data

(63) Continuation-in-part of application No. 13/870,669, filed on Apr. 25, 2013, now Pat. No. 9,130,070.

(51) Int. Cl.
*H03F 3/08* (2006.01)
*G01R 27/26* (2006.01)
(Continued)

(52) U.S. Cl.
CPC .............. *H03F 3/08* (2013.01); *A61B 5/0059* (2013.01); *A61B 5/02433* (2013.01);
(Continued)

(58) Field of Classification Search
CPC ........ H03F 3/08; H03F 3/087; H03F 3/45475; A61B 5/0059; A61B 5/02433;
(Continued)

(56) References Cited

U.S. PATENT DOCUMENTS 5,684,294 A 11/1997 Kouhi
5,739,652 A 4/1998 Sriram
(Continued)

FOREIGN PATENT DOCUMENTS

EP 2549248 1/2013
KR 11-506544 6/1999
(Continued)

OTHER PUBLICATIONS

OA1 issued in KR Patent Application Serial No. 10-2014-48009 dated Feb. 25, 2016, 7 pages.
(Continued)

*Primary Examiner* — Georgia Y Epps
*Assistant Examiner* — Don Williams
(74) *Attorney, Agent, or Firm* — Patent Capital Group (57) ABSTRACT

An electrical circuit includes a sensor configured to generate a current signal comprising a first portion comprising a contribution from a target source and/or a second portion comprising a contribution from sources other than the target source, a trans-impedance amplifier that amplifies the current signal and generate a low noise signal, and a high pass filter that converts the low noise signal into an AC signal having a positive amplitude, a negative amplitude, and a zero cross-over point between the positive and negative amplitudes. The circuit also includes a positive integrating amplifier that receives the positive amplitude of the AC signal and generates a positive integrated value over an integration period, and a negative integrating amplifier that receives the negative amplitude of the AC signal and generates a negative integrated value over the integration period. The circuit further includes at least one analog-to-digital converter that receives the integrated values.

20 Claims, 6 Drawing Sheets

(51) Int. Cl.
| | |
|---|---|
| *G01R 33/02* | (2006.01) |
| *G06F 3/01* | (2006.01) |
| *A61B 5/00* | (2006.01) |
| *A61B 5/024* | (2006.01) |
| *H01L 31/02* | (2006.01) |
| *H03F 3/45* | (2006.01) |

(52) U.S. Cl.
CPC ............ *A61B 5/7225* (2013.01); *G01R 27/26* (2013.01); *G01R 27/2605* (2013.01); *G01R 33/02* (2013.01); *G06F 3/017* (2013.01); *H01L 31/02019* (2013.01); *H03F 3/087* (2013.01); *H03F 3/45475* (2013.01); *H04B 2210/003* (2013.01)

(58) Field of Classification Search
CPC .. A61B 5/7225; G01R 27/26; G01R 27/2605; G01R 33/02; G06F 3/017; H01L 31/02019; H04B 2210/003
See application file for complete search history.

(56) References Cited

U.S. PATENT DOCUMENTS

| | | | |
|---|---|---|---|
| 7,960,679 | B2 | 6/2011 | Fann |
| 7,978,311 | B2 | 7/2011 | Deliwala |
| 9,130,070 | B2 | 9/2015 | Deliwala |
| 2005/0258885 | A1 | 11/2005 | Ono |
| 2007/0080905 | A1 | 4/2007 | Takahara |
| 2009/0127461 | A1 | 5/2009 | Holcombe et al. |
| 2010/0087718 | A1* | 4/2010 | Gonopolskiy ..... A61B 5/14551 600/323 |
| 2011/0114842 | A1 | 5/2011 | Ji et al. |
| 2011/0163233 | A1 | 7/2011 | Ng et al. |
| 2011/0186714 | A1 | 8/2011 | Hung et al. |
| 2014/0285472 | A1 | 9/2014 | Raynor |
| 2014/0323844 | A1 | 10/2014 | Deliwala et al. |
| 2014/0323874 | A1 | 10/2014 | Addison et al. |
| 2016/0025777 | A1 | 1/2016 | Deliwala |

FOREIGN PATENT DOCUMENTS

| | | |
|---|---|---|
| KR | 10-1701560 | 2/2017 |
| WO | 98/18205 | 4/1998 |
| WO | 2016/015033 | 1/2016 |

OTHER PUBLICATIONS

English Summary of OA1 issued in KR Patent Application Serial No. 10-2014-48009 dated Feb. 25, 2016, 5 pages.
U.S. Appl. No. 13/870,669, filed Apr. 25, 2013.
1st Action Notice of Allowance issued in U.S. Appl. No. 13/860,669 dated Apr. 28, 2015, 11 pages.
Models 1601 and 1611 User's Manual, "High-Speed Photoreceivers", 12 pages.
G. Lochead, "Photodiode Amplifiers", 8 pages.
Chirag J. Pujary, "Investigation of Photodetector Optimization in Reducing Power Consumption by a Noninvasive Pulse Oximeter Sensor", Jan. 16, 2004, 133 pages.
Humaira Taz, "Radon Detection Using a PIN Photodiode", Wesleyan College, 16 pages.
Patrick J. Windpassinger et al., "Ultra Low-Noise Differential Ac-Coupled Photodetector for Sensitive Pulse Detection Applications", Measurement Science and Technology 20 (2009) 0957-0233/ 09/055301, 2009 IOP Publishing Ltd., 7 pages.
"Integrated Photodiode and Amplifier", Burr-Brown, OPT201, 1993 Burr-Brown Corporation, PDS-1180B, Jan. 1995, 11 pages.
"Photodiode Typical Operating Circuits", AP Technologies, www.aptechnologies.co.uk, 2 pages.
David Westerman, "Understand and Apply the Transimpedance Amplifier" (Part 1 of 2), Planet Analog, Aug. 8, 2007, 8 pages.
"Designing Photodiode Amplifier Circuits With OPA128", Burr-Brown, AB077, 1994 Burr-Brown Corporation, Jan. 1994, 4 pages.
"SHM-180—Eight Channel Sample & Hold Module", Becker & Hickl GmbH, Apr. 2003, 13 pages.
"Application Circuit Examples of Si Photodiode", Hamamatsu Photonics K.K., Solid State Division, Jun. 2004, 4 pages.
English Translation of Letters Patent for KR10-2014-0048009 dated Feb. 1, 2017.
Ex-Parte Quayle Office Action issued in U.S. Appl. No. 14/808,148 dated Oct. 26, 2016, 9 pages.
Notice of Allowance issued in U.S. Appl. No. 14/808,148 dated Dec. 21, 2016, 7 pages.
International Search Report and Written Opinion issued in PCT Patent Application Serial No. US/2015/042148 dated Dec. 3, 2015, 8 pages.
Notice of Allowance issued in U.S. Appl. No. 14/808,148 dated Apr. 14, 2017, 10 pages.
Search Report issued in EP Patent Application Serial No. 15825236.1 dated Mar. 20, 2018, 10 pages.
DE Office Action issued in DE Patent Application Serial No. 102014105398.2 dated May 14, 2018, 10 pages.
EN Translation of DE Office Action issued in DE Patent Application Serial No. 102014105398.2 dated May 14, 2018, 3 pages.
Brett A. Warneke et al., *An Autonomous 16 mm3 Solar-Powered Node for Distributed Wireless Sensor Networks*, 7803-7454-1/02 © 2002 IEEE, 6 pages.
J. M. Monzó et al., *Accurate Simulation Testbunch for Nuclear Imaging Systems*, © 2008 IEEE Transactions on Nuclear Science, vol. 55, Issue 1, 7 pages.

\* cited by examiner

FOUR-STAGE CIRCUIT ARCHITECTURE FOR DETECTING PULSED SIGNALS

CROSS-REFERENCE TO RELATED APPLICATIONS

This application is a continuation-in-part and claims benefit of U.S. Original patent application Ser. No. 13/870,669 filed 25 Apr. 2013 entitled "FOUR-STAGE CIRCUIT ARCHITECTURE FOR DETECTING PULSED SIGNALS", which is incorporated herein by reference in its entirety.

FIELD OF THE DISCLOSURE

This disclosure relates in general to the field of electronic devices and, more particularly, to a circuit architecture for current detectors.

BACKGROUND

A photodiode is a type of photo-detector capable of converting light into current or voltage. Generally, the photodiode is a semiconductor device with a PIN or PN connection structure. When a photon of sufficient energy strikes the photodiode, it excites electrons, creating free electrons and positively charged electron holes. The holes move toward the anode, and electrons toward the cathode, and a photocurrent is produced proportional to the amount of incident light on the photodiode.

Other types of sensors include e.g. pyro-electric, piezo-electric, or capacitive sensors.

All of these sensors are common in that they include a pair of electrodes and, when stimulated by their respective stimuli, the state of charge across the electrodes changes. Current resulting from the changed state of charge across the electrodes can then be used to detect and quantify the stimuli. For example, a photodiode produces a change in the state of charge across its electrodes when the light is incident on the photodiode. In other words, the photodiode generates current (which may be referred to as "photocurrent") in the presence of light, where the current is proportional to the amount of light incident on the photodiode. Similarly, a pyro-electric sensor produces a change in the state of charge across its electrodes when heated or cooled, a piezo-electric sensor produces a change in the state of charge across its electrodes in response to the change in its mechanical orientation (e.g. strain), while a capacitive sensor is one where changes in the environment change the effective capacitance of the sense element, which in turn changes the capacity to hold charge.

For such sensors, as well as other sensors operating according to similar principles of detecting change of charge state, it may be desirable to be able to detect and quantify stimuli originating from a specific source of interest as well as stimuli originating from all other sources besides the source of interest. For example, in context of a photodiode, it may be desirable to detect and quantify a contribution to the current generated by the photodiode that is due to the detection of light generated by a particular light source of interest, e.g. a particular light emitting diode (LED), as well as to detect and quantify contribution to the photocurrent that is due to the detection of light generated by all other light sources besides this light source of interest.

SUMMARY OF THE DISCLOSURE

An example electrical circuit is provided and includes a sensor configured to generate a current signal, the current signal comprising at least a first portion comprising a contribution from a target source and/or a second portion comprising a contribution from one or more sources other than the target source, and four stages. The first stage comprises a trans-impedance amplifier configured to amplify the current signal and generate a low noise signal. The second stage comprises a high pass filter configured to convert the low noise signal into an alternating current (AC) signal having a positive amplitude, a negative amplitude, and a zero cross-over point between the positive amplitude and the negative amplitude. The third stage comprises a positive integrating amplifier configured to receive the positive amplitude of the AC signal and generate a positive integrated value over an integration period and a negative integrating amplifier configured to receive the negative amplitude of the AC signal and generate a negative integrated value over the integration period. The fourth stage comprises at least an analog-to-digital converter (ADC) configured to receive the positive and negative integrated values and generate a digital value indicative of the first portion of the current signal based on the positive and negative integrated values.

In various embodiments, the contribution to the current signal from the target source comprises a pulse or a series of repeating pulses.

In various embodiments, the sensor may include one or more of a photodiode, a capacitance sensor, an impedance sensor, a magnetic field sensor, and a piezo-electric film.

In an embodiment, the target source comprises a target light source, the sensor comprises a photodiode, the current signal comprises a photocurrent signal, and the electrical circuit is coupled to a photoplethysmography system. Light from the light source reflects off, or transmits through an organ before reaching the photodiode, such that the photocurrent signal from the photodiode can provide an indication of a measurement of the organ. The photoplethysmography system does not have to include a light blocking enclosure to keep out ambient light for accurate measurements.

As will be appreciated by one skilled in the art, aspects of the present disclosure may be embodied in various manners—e.g. as a method, a system, a computer program product, or a computer-readable storage medium. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Functions described in this disclosure may be implemented as an algorithm executed by one or more processing units, e.g. one or more microprocessors, of one or more computers. In various embodiments, different steps and portions of the steps of each of the methods described herein may be performed by different processing units. Furthermore, aspects of the present disclosure may take the form of a computer program product embodied in one or more computer readable medium(s), preferably non-transitory, having computer readable program code embodied, e.g., stored, thereon. In various embodiments, such a computer program may, for example, be downloaded (updated) to the existing devices and systems (e.g. to the existing current detection modules or controllers of such modules, etc.) or be stored upon manufacturing of these devices and systems.

Other features and advantages of the disclosure are apparent from the following description, and from the claims.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION

Embodiments of the present disclosure are based on the use of a current detection module capable of differentiating and quantifying (i.e. measuring) the contribution to the current signal generated by a certain source of interest from contributions from sources other than the predefined source of interest, i.e. ambient sources. As long as the contribution to the current signal from the predefined source comprises a pulsed signal (referred to in the following as "pulse(s) of interest"), the current detection module is configured to synchronize itself to the pulse(s) so that there is a predetermined phase relationship between the pulse(s) and functions carried out by various stages of the current detection module (referred to in the following as a "receiver circuit"). The pulsed signal of the source of interest may include one pulse or multiple pulses, where a pulse may include one or more frequency components. Ambient sources may also contain multiple frequency components, possibly even the same components as those of the pulse of the predefined source of interest. Because the frequencies present in the pulse(s) of interest are synchronized to the receiver circuit (i.e. synchronized to the clock of the current detection module), there is a certain known phase relationship between the current detection module and each of the frequency components of the pulse of interest (which phase relationship could be different for different frequencies in the pulse of interest, but nevertheless known ahead of time). The current detection module is designed to detect pulses synchronously and in a way that requires precise phase relationship between the receiver circuit and the source of interest. While the ambient sources may contain the same frequency components as the source of interest, the ambient sources are unlikely to contain precisely the same amplitudes and phases that make up the pulses of interest (i.e. ambient sources are unlikely to be synchronized to the current detection module). As a result, frequencies present in the ambient are averaged out even if the ambient sources contain very similar or the same frequencies as the pulse of interest.

Much of prior art approaches where it is desired to detect and measure contribution from a predefined source of interest from all other possible sources is based on avoiding interference with the ambient source by choosing a frequency of the source of interest to be different than the frequencies present in the ambient. Inventors of the present application realized that such approaches are not always successful because the content of the ambient is often unpredictable. Inventors of the present application further realized that by synchronizing the receiver circuit to the pulses of the signal of interest, it is possible to detect and measure contributions from the source of interest in presence of contributions from one or more ambient sources without having to choose frequencies for the pulses of the signal of interest that are different from the ambient (i.e. the frequency components could be the same).

An exemplary current detection module and functionality of such a module is now described in greater detail with reference to measurement of photocurrent signal generated by a photodiode in response to detecting light from a light source (i.e. for the example that the current detection module is used to detect photocurrent). However, teachings provided herein are equally applicable to current detection modules configured to detect currents generated by sensors, or charge generators, other than photodiodes, such as, but not limited to, pyro-electric, piezo-electric, or capacitive sensors. For all of these sensors (i.e. some kind of charge generators), a general setting described below for photodiodes is applicable where a sensor generates a current signal that may contain contributions from what may be considered as two "sources." One "source" is a particular source of interest (i.e. the sensor sensing some event of interest—e.g. light generated by a particular LED as detected by a photodiode, change in temperature due to a particular source of interest detected by a pyro-electric sensor, mechanical deformation caused by a particular force/source of interest as detected by a piezo-electric sensor, touch by e.g. a human or a stylus as detected by a capacitance sensor, etc.). The other "source" may be considered to include everything else besides the source of interest that may cause the change in the charge state of the sensor. Such a source is referred to as an "ambient source." In other words, the same sensor that senses contributions from the source of interest may also (or instead of, in case the source of interest is not providing any contribution) sense other things—e.g. the photodiode may detect ambient light, the capacitance sensor may sense touch that is not by a human or a stylus, etc. One common goal for all of these sensors may be to be able to distinguish and quantify these separate contributions to the current generated by the sensors.

Referring now to the example of a photodiode as a sensor, some embodiments of the present disclosure provide for measurement of photocurrent signal from a light source, which may be synchronized (e.g., specifically modulated).

Common photodiode circuits (e.g., photodiode amplifiers) are typically configured for one of low noise, wide bandwidth, and high dynamic range. Such circuits do not generally provide all three characteristics (low noise, wide bandwidth, and high dynamic range) simultaneously. Even if some circuits do provide all three characteristics, such circuits may require high power, or may not provide for high signal extraction of a target light source (especially in the presence of a high amount of ambient light, which is considered an interference and acts like noise), or may not be flexible to accommodate different sampling modes or multiple channels.

For example, Burr Brown's OPT201 integrated photodiode and amplifier provides low noise operation, but does not have any means to distinguish between different types of light sources. In another example, New Focus Inc.'s 1601 and 1611 high-speed photo-receivers have large gain bandwidth (GBW), low noise, high drive capability and large dynamic range to enable wide bandwidth low-noise detection of signals distributed over fiber-optic cables, or found in applications such as high resolution spectroscopy, fiber-optic sensors, and optical metrology. The photo-receivers consist of a silicon or InGaAs PIN photodiode followed by a low-noise amplifier. However, these photo-receives are not capable of sampling multiple channels, and are designed such that there is no need to distinguish between different types of light that fall on the sensor—predefined source of interest and the ambient.

Figure 1:
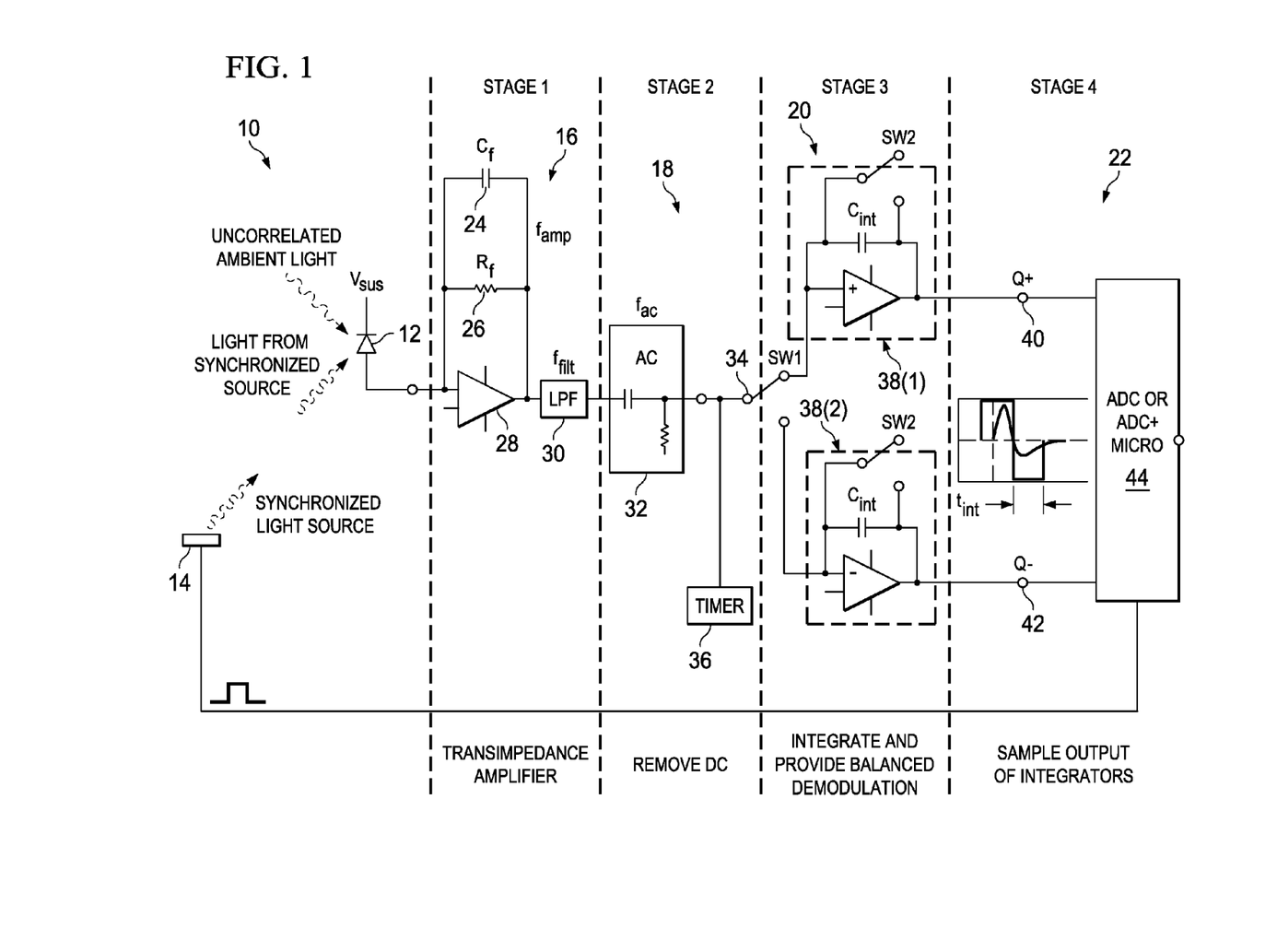
FIG. 1 is a simplified circuit diagram of a circuit architecture for photodiodes in accordance with one embodiment.

Turning to FIG. 1, FIG. 1 is a simplified block diagram of electrical circuit 10 that implements circuit architecture for photodiodes. Electrical circuit 10 is configured to simultaneously provide low-noise and low-power consumption (among other features) while avoiding interference from uncorrelated light sources (e.g., sunlight, background light, ambient light) in the environment. Furthermore, the circuit architecture is configured to have high dynamic range that is suitable for use in the presence of a strong light source such as sunlight. The circuit architecture can be extended to multiple channels, for example, in applications that involve reading multiple photodiode signals concurrently.

According to various embodiments, electrical circuit 10 can provide the following features substantially simultaneously: low noise; high dynamic range; high rejection of uncorrelated light sources or ambient light; high signal extraction of a locked or target light source; low power operation; simultaneous sampling of multiple channels for analog-to-digital conversion, which can improve ambient light rejection (ALR) in many cases, when a sensor is a photodiode, and allow the use of relatively slower and more precise analog-to-digital converters (ADCs); and flexibility for different sampling modes.

According to a specific embodiment, electrical circuit 10 may comprise a sensor 12 that detects a stimuli from a target source of interest 14, e.g. a photodiode 12 that receives light from a light source 14. The current signal generated by the sensor 12 can include a single pulse of low duty cycle or a multiple pulse train of low duty cycle (e.g., depending on the duty cycle of target source 14). In some embodiments, the target source 14 may be modulated by an integrated circuit (not shown) coupled to electrical circuit 10.

According to various embodiments, electrical circuit 10 can comprise four stages 16, 18, 20, and 22. Stage 16 can include a trans-impedance amplifier (TIA), which may amplify the current signal from the sensor 12 and generate a low noise signal. The trans-impedance amplifier can also convert the current signal to a voltage at the output. Stage 16 includes a feedback capacitance 24 ($C_f$) in parallel with a feedback resistor 26 ($R_f$) connected to an operational amplifier (op-amp) 28 in an R-C feedback loop, for example, to reduce noise and stabilize the circuit.

Any source of interest 14 (including DC source, e.g. DC light for the example of a sensor being a photodiode) whose bandwidth is within the amplifier bandwidth may be amplified by amplifier 28. Generally, capacitance of photodiodes can affect noise gain based on the relative value of the capacitance to resistance value $R_f$ of feedback resistor 26 and capacitance value $C_f$ of feedback capacitor 24. Configuring stage 16 as a first stage can provide increased flexibility to minimize excess noise gain. In a general sense, two dominant noise sources in electrical circuit 10 include Johnson noise of feedback resistor 26 and amplifier 28's input voltage noise. To reduce Johnson noise, resistance value $R_f$ of feedback resistor 26 can be chosen to be as large as possible consistent with the largest DC photocurrent that is expected for a given arrangement of photodiode 12 and other components. Such a configuration may provide minimum amplifier noise consistent with the total DC photocurrent. Capacitance value $C_f$ of feedback capacitor 24 can be chosen to change the bandwidth of the photocurrent signal (which may be of the order of approximately $1/\tau$, where $\tau$ is the input pulse duration) as desired. Stage 16 can also include a low pass filter (LPF) 30 that additionally filters out high frequency noise in the photocurrent signal. LPF 30 can also increase the duration of pulses of the photocurrent signal (which may coincide with the pulse duration of the (synchronized) target source 14). The frequency threshold of LPF 30 can be configured as desired based on particular needs depending on the expected (or measured) noise characteristics.

Stage 18 may comprise a high pass filter (active or passive) including an AC power source 32 (with frequency $f_{ac}$) and a capacitor that provides AC coupling. Stage 18 can eliminate low frequencies (e.g., remove DC) and allow high gain to be provided in subsequent stages. AC input 32 that can change the DC component of the photocurrent signal to AC, thereby providing a zero cross-over point where the amplitude of the photocurrent signal changes from positive to negative. Stage 18 can eliminate some of the noise components from stage 16 and high frequency noise and lower frequency photocurrents from ambient light (or uncorrelated light sources).

In some embodiments, a square pulse shaped signal from target source 14 may be modified by the filtering action of LPF 30 and stage 18 to eliminate low frequencies. The corner frequencies (e.g., boundary in the frequency response at which energy flowing through begins to reduce (attenuate or reflect)) of stages 16 and 18 may be chosen to maximize signal measurement and provide ALR. For example, the corner frequency of the high pass filter of stage 18 can be set as large as $0.5/\tau$. The choice can also be influenced by the integration time chosen in next stage 20.

Stage 20 may comprise integration and demodulation. A single pole changeover switch 34 may switch the incoming signal based on a clock from timer 36. The clock cycle of timer 36 may be configured to match the zero cross-over point of the photocurrent signal from stage 18. When the zero cross-over point occurs, switch 34 may switch from integrating amplifier 38(1) to integrating amplifier 38(2). Two integrating amplifiers 38(1) and 38(2) may be used to integrate in succession on the positive portion of the signal from stage 18 when switch 34 is connected to the positive integrating amplifier 38(1) and on the negative portion of the signal from stage 18 when switch 34 is connected to the negative integrating amplifier 38(2). Each of positive integrating amplifier 38(1) and negative integrating amplifier 38(2) may include a capacitor $C_{int}$ configured to enable the operational amplifier therein to operate as an integrator. In some embodiments, switches SW2 may be used to reset positive integrating amplifier 38(1) and negative integrating amplifier 38(2), for example, after every conversion cycle or after multiple integration phases.

Each of positive integrating amplifier 38(1) and negative integrating amplifier 38(2) (generally referred to individually as integrator 38) acts like a storage element that produces an output voltage output proportional to the integral of its input current (converted from voltage output of the previous stage) over time. In other words, the magnitude of the output voltage is determined by the length of time (integration period $t_{int}$) during which an input voltage is present as the current through the feedback loop (comprising $C_{int}$) charges or discharges capacitor $C_{int}$. The circuit operates by passing a current that charges capacitor $C_{int}$ over time from the input current of stage 18. When the input current of stage 18 is firstly applied to the integrator, the feedback capacitor $C_{int}$ begins to charge and the output voltage is determined by the total charge (which is the integral of the input current over time).

Positive integrating amplifier 38(1) may generate a positive integrated value 40 ($Q_+$), which is the integral over time of the positive amplitude of the alternating current signal from stage 18, and negative integrating amplifier 38(2) may generate a negative integrated value 42 ($Q_-$), which is the integral over time of the negative amplitude of the alternating current signal from stage 18. The integration period $t_{int}$ can be configured over a wide range based on particular needs. The start of the integration cycle may be controlled by timer 36 in a microcomputer, a simple programmable circuit, or other suitable component. The gain of the amplifier can be chosen to optimize conversion by an analog-to-digital convertor (ADC) 44 (as DC and low frequency components of ambient light are largely removed after stage 18) at stage 22. At the end of the positive and negative integration cycle, substantially all photocurrents in the integration period $t_{int}$ may be integrated and the voltage may be held at the outputs of stage 20. The voltages may be subtracted either before conversion by a difference amplifier or converted by ADC 44 and then subtracted digitally.

Mathematically, the integration and subtraction are similar to a low pass filter and a "lock-in" filter to further remove noise artifacts of the ambient light while amplifying the photocurrent signal. For example, the phase of switch 34 can be adjusted to provide "lock-in" functionality to a signal originating from a distant system. Assume, merely for illustrative purposes, and not as a limitation, that a distant light source produces a train of N pulses repeating at a rate R. Timer 36 can be configured to lock to the phase of the clock that generates the N pulses. Thus a phase lock loop can be constructed to measure the light intensity of the distant light source. Positive integrating amplifier 38(1) and negative integrating amplifier 38(2) can together provide increased ALR. Outputs 40 and 42 may be fed to ADC (or ADC integrated with a micro-controller) 44 at stage 22 to perform further operations.

ADC 44 can read the output voltage of stage 20 and a controller therein can reset integrators 38(1) and 38(2), for example, by momentarily closing SW2, to start a new integration cycle. The reset can occur at the end of each pulse or at the end of a group of pulses. The voltage at stage 20 may represent a signal charge deposited at sensor 12 in addition to charge from substantially all ambient interference. In an example embodiment, the pulses may be added together thereby increasing signal strength and reducing noise and interference digitally after ADC 44. In another example embodiment, the pulses may be added in an analog domain until SW2 resets integrating capacitors $C_{int}$. Embodiments of electrical circuit 10 can permit extension of the circuit architecture to ultra short pulses, for example in nanosecond and picosecond domain, without substantially increasing the speed of ADC 44. High dynamic range may be facilitated as digital additions of pulses can be carried out over many more pulses, almost without limit, than any analog addition on the integrating capacitors $C_{int}$ would permit.

According to various embodiments, input current generated by sensor 12 may be converted to voltage at stage 16. Any frequency content of the voltage signal may be shaped by the band pass filtering functions at state 18. The output voltage of stage 18 may be converted back to current, for example, using a suitable resistor, and integrated with capacitor $C_{int}$ over time $t_{int}$ over positive and negative cycles. At least a portion of the behavior of electrical circuit 10 may be indicated by the following equations:

$$V_{TIA} = i_p \times R_f$$

$$V_{ac} = BPF(f_{filt}) \times V_{TIA}$$

$$V_{int} = \left(\frac{V_{ac}}{R_{in}}\right) \times (C_{int} \times t_{int})$$

where $V_{TIA}$ is the output voltage at stage 16; $i_p$ is the photovoltaic current; $R_f$ is the resistance of feedback resistor 26; $V_{ac}$ is the output voltage at stage 18; $BPF(f_{filt})$ is a bandpass filter shaping function of stage 18; $V_{int}$ is the output voltage at stage 20; $R_{in}$ is the resistance of a resistor (not shown) at stage 20; $C_{int}$ is the capacitance at stage 20; and $t_{int}$ is the integration time.

For example, Rf may be chosen to prevent saturation at stage 16 with a high amount of low frequency ambient sources, such as e.g. sunlight. The corner frequencies can be chosen to minimize interference while transmitting most of the signal pulse at stage 18. Moreover, the choice of $R_{in}$ and $C_{int}$ can allow signal gain at stage 20 to match ADC input range at stage 22. Further, multiple cycles of analog integration over many pulses with digital integration at ADC 44 can allow a large dynamic range.

In some embodiments, an intense short pulse produced by target source 14 may perform better for low power operation as the system of amplifiers and ADC can be powered down between the pulses. Also, for the same net power consumed by synchronous target source 14, signal-to-noise-ratio (SNR) can be maximized by using the shortest possible pulse that can be produced by a driver circuit. (The shortest possible pulse may be limited by the peak current output available.) Electrical circuit 10 may be dynamically or programmatically configured in some embodiments, for example, by changing the $C_f$, $R_f$, $C_{int}$, and other passive component values and corner frequency values as desired.

In some embodiments, the low frequency (e.g., DC) component of the current signal generated by sensor 12 may be measured by directly connecting stage 16 to the input of ADC 44. Alternatively, the low frequency component may be measured by connecting stage 16 to either positive integrating amplifier 38(1) or negative integrating amplifier 38(2) of stage 20. In embodiments with low levels of ambient signals, one of positive and negative integrating amplifiers 38(1) and 38(2), respectively, may be connected directly to sensor 12, bypassing stages 16 and 18.

According to various embodiments, at least some components of stages 16, 18, and 20 are programmable (e.g., component values adjustable according to user specifications) after electrical circuit has been implemented in a physical form. The component values may be programmable manually, or by a suitable computing device or controller. For example, capacitance $C_f$ of feedback capacitor 24, resistance $R_f$ of feedback resistor 26; bandpass filter shaping function $BPF(f_{filt})$, resistance $R_{in}$, capacitance $C_{int}$ etc. can be programmed according to the application in which electrical circuit 10 is to be used. Thus, the same physical representation of electrical circuit 10 may have a first set of component values in one application (e.g., photoplethysmography system used in controlled ambient light) and a different, second set of component values in a different application (e.g., wireless sensor used in uncontrolled ambient light).

Figure 2:
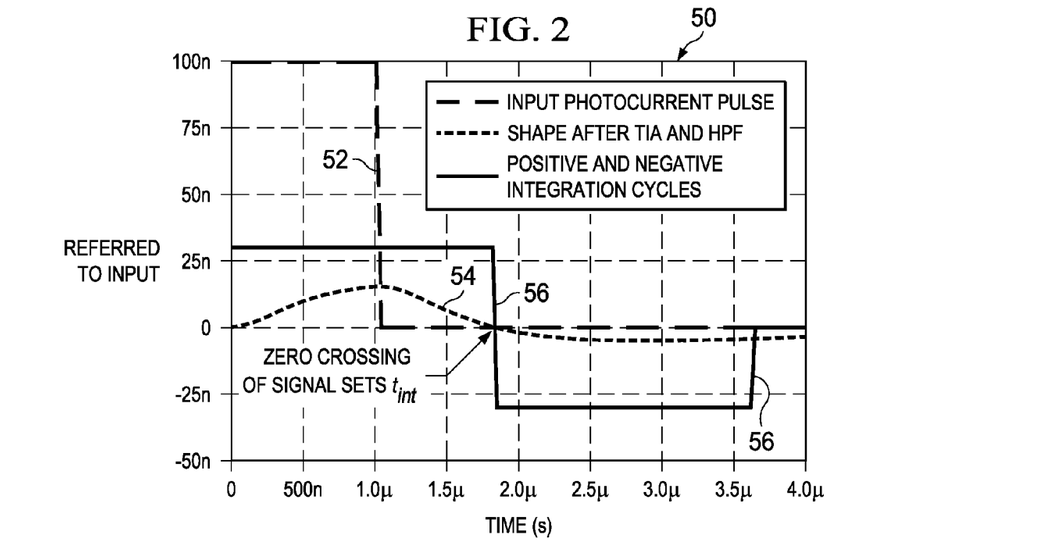
FIG. 2 is a simplified diagram illustrating example details of measurements associated with the circuit architecture according to an embodiment.

Turning to FIG. 2, FIG. 2 is a simplified diagram illustrating an example signal chart 50 according to an embodiment of electrical circuit 10. Merely for example purposes, and not as a limitation, the pulse duration $\tau$ was set at 1 µs, and the high pass filter corner frequency (of stage 18) was set at 300 kHz or $0.3/\tau$. The output of the stages was referred to the input to allow for easy comparison. Input photocurrent pulse 52 from synchronized light source may result in a photocurrent signal 54, illustrated after stages 16 and 18. Signal 54 indicates an AC signal, with a zero cross-over point. The zero cross-over point may set the integrating cycle duration $t_{int}$. Positive and negative integration cycles may be denoted by a line 56, which also has a zero cross-over point coinciding with the zero cross-over point of signal 54.

Figure 3:
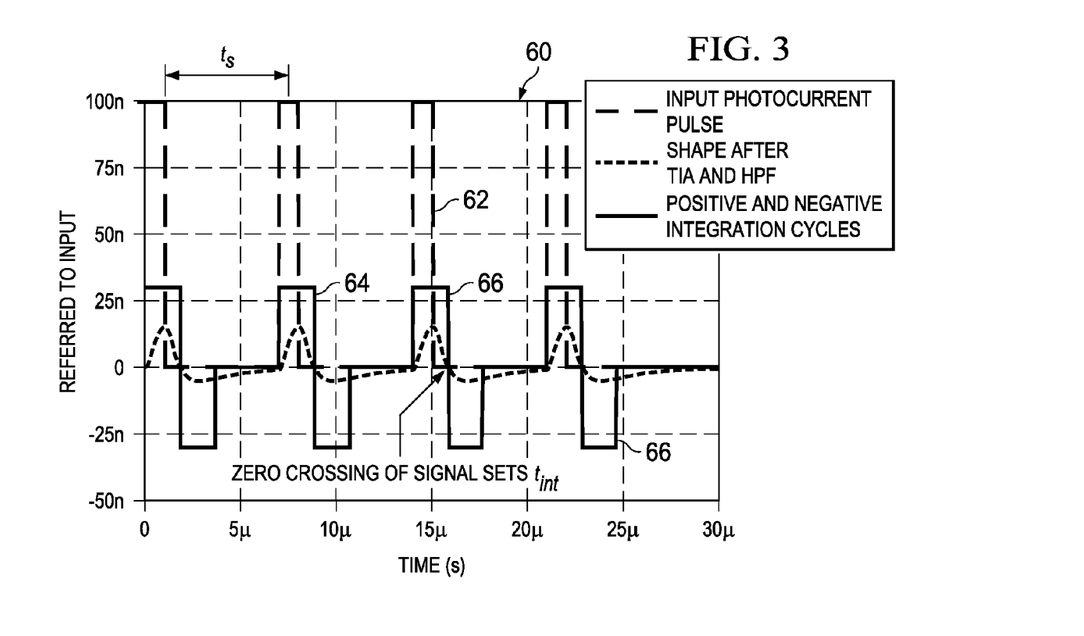
FIG. 3 is a simplified diagram of other example details of measurements associated with the circuit architecture according to an embodiment.

Turning to FIG. 3, FIG. 3 is a simplified diagram illustrating an example signal chart 60 according to an embodiment of electrical circuit 10. Input photocurrent pulse 62 from synchronized light source may result in a photocurrent signal 64, illustrated after stages 16 and 18. Signal 64 is an AC signal, with a zero cross-over point. The zero cross-over point may set the integrating cycle duration $t_{int}$. Positive and negative integration cycles may be denoted by the line 66, which also has a zero cross-over point coinciding with the zero cross-over point of signal 64. Input photocurrent signal 62 may be generated as pulses (e.g., with a short 1 µs pulse). Each pulse of signal 64 may be shaped by the action of stages 16 and 18. Positive and negative integration cycles are applied to each pulse in the train of pulses. The separation $t_s$ between pulses may be configured based on the settling time or to minimize any effect of particularly dominant frequency components (if any) from ambient light.

Figure 4:
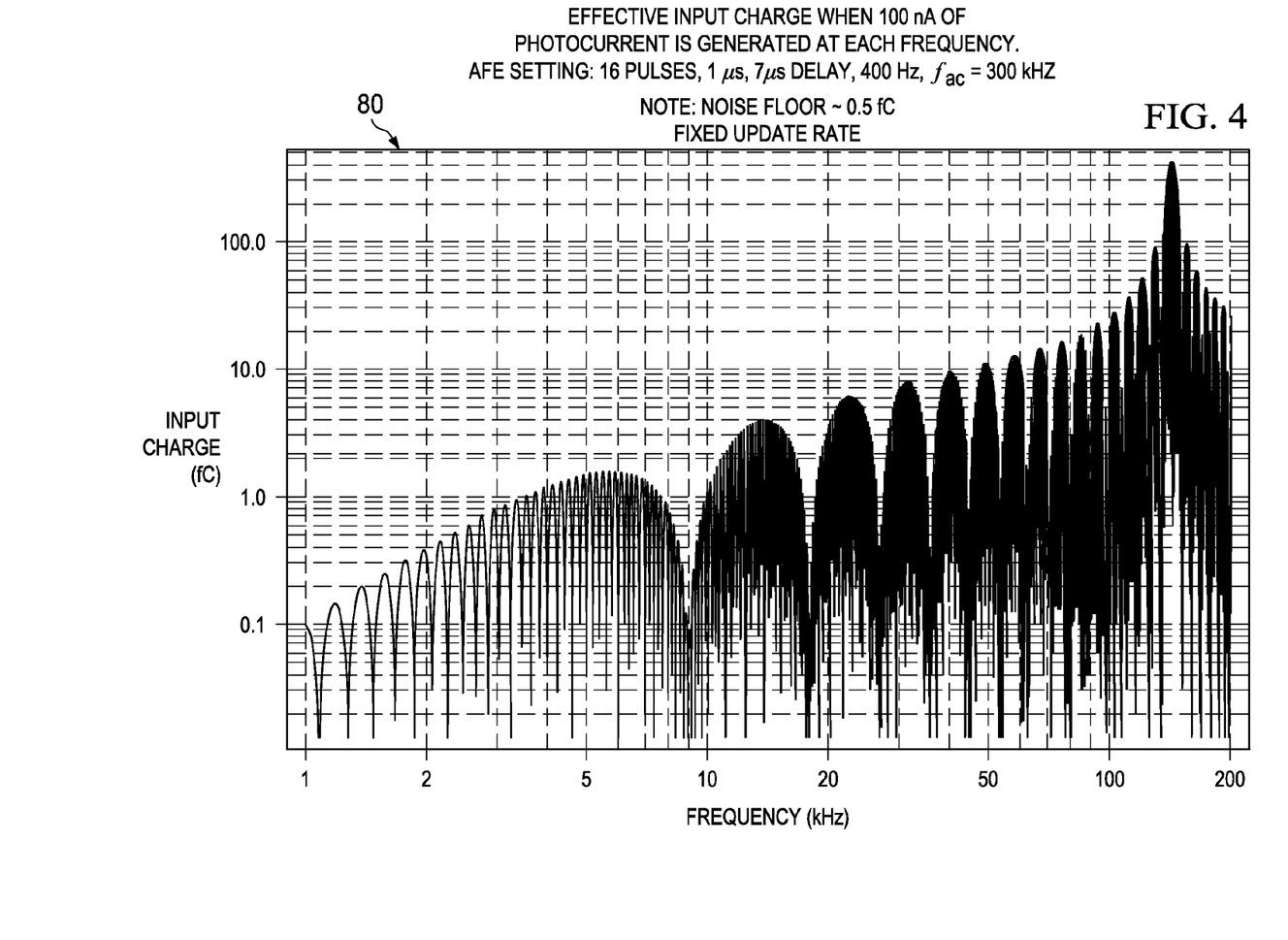
FIG. 4 is a simplified diagram of yet other example details of measurements associated with the circuit architecture according to an embodiment.

Turning to FIG. 4, FIG. 4 is a simplified diagram illustrating a graph 80 showing input charge over frequency of interfering ambient light. Graph 80 illustrates the suppression of ambient light according to electrical circuit 10. Assume, merely for illustrative purposes, and not as a limitation, that a light source in the environment has a frequency f. Further assume that the phase of the ambient light is somehow synchronized to produce worst case interference at each possible frequency of the ambient light (indicated along the x-axis). The measured amplitude of the photocurrent signal produced at that frequency can be reduced by the action of all four stages 16, 18, 20 and 22. In the case of a train of multiple pulses, suppression may be increased even further.

Graph 80 was generated using 16 pulses, and the input referred integrated current (after stage 22) was calculated as charge on the Y-axis. According to embodiments of electrical circuit 10, ALR of almost a factor of 100 at frequencies below 50 kHz may be observed. Many ambient light sources such as fluorescent lamps and light emitting diode (LED) lights have components at low frequencies. Very low frequencies such as 120 Hz may be suppressed by factors exceeding 1000 and DC light may be completely blocked.

It may be noted that embodiments of electrical circuit 10 may reject electrical noise injected at sensor 12 similar to rejection of currents generated by ambient sources. Indeed, components of electrical circuit 10 may not distinguish between currents generated by the sensor in response to stimuli of ambient sources or electromagnetic interference (EMI) or any other electrical noise injected into the circuit, facilitating robustness in the presence of both electrical interference and interference due to detection by the sensor of ambient source (e.g. optical interference for the example of sensor 12 being a photodiode).

Figure 5:
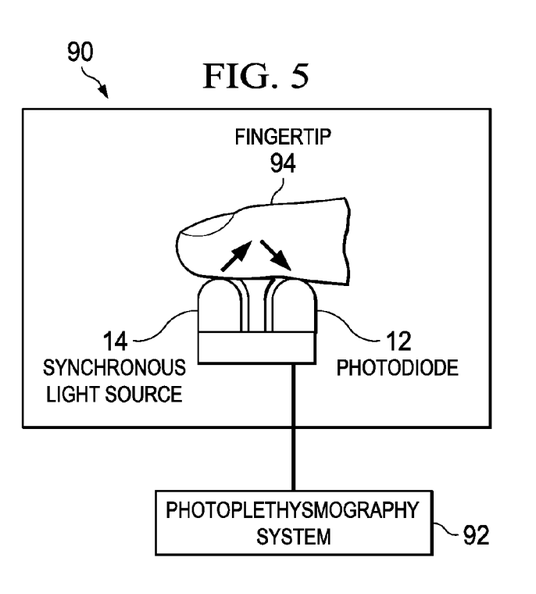
FIG. 5 is a simplified diagram of an example detail of an application associated with the circuit architecture according to an embodiment.

Turning to FIG. 5, FIG. 5 is a simplified diagram illustrating an example application 90 of electrical circuit 10 as used in a photoplethysmography system 92. A photoplethysmograph is a device used to optically measure changes in the effective light transmission or reflectance of an organ. Examples of photoplethysmography systems include pulse oximeters, cardiovascular monitors, and respiration detectors. Application 90 illustrated in the FIGURE can include a pulse oximeter, although electrical circuit 10 may be implemented in any other type of photoplethysmography systems as well, within the broad scope of the embodiments.

The pulse oximeter of application 90 may include photodiode 12 and synchronous light source (e.g., red and infrared light emitting LED) connected to photoplethysmography system 92, which can include electrical circuit 10 and other components, based on the particular application need. The pulse oximeter may be attached to, or otherwise placed in proximity with an organ (e.g., fingertip) 94 (e.g., of the patient whose pulse is being monitored). Light emitted by synchronous light source 14 may be partially reflected, transmitted, absorbed, and/or scattered by the organ (e.g., skin, surrounding tissues, and the blood at the fingertip) before it reaches photodiode 12. The photocurrent signal from photodiode 12 can provide a measurement of the organ, for example, indicative of pulse rate, or oxygen content, etc.

Currently available pulse oximeters and other photoplethysmography systems use caps, light proof enclosures, and other such devices to prevent ambient/background light from generating noise in the photoplethysmography systems. With electrical circuit 10, such light blocking enclosures (e.g., caps, boxes, etc.) need not be used, as electrical circuit 10 includes noise reduction capabilities sufficient to overcome ambient and other background light noise. Moreover, because of the noise reduction characteristics of electrical circuit 10, and its consequent reduced sensitivity to ambient and DC light, the distance between synchronous light source 14 and photodiode 12 may be configured based on convenience factors, rather than noise reduction.

Figure 6:
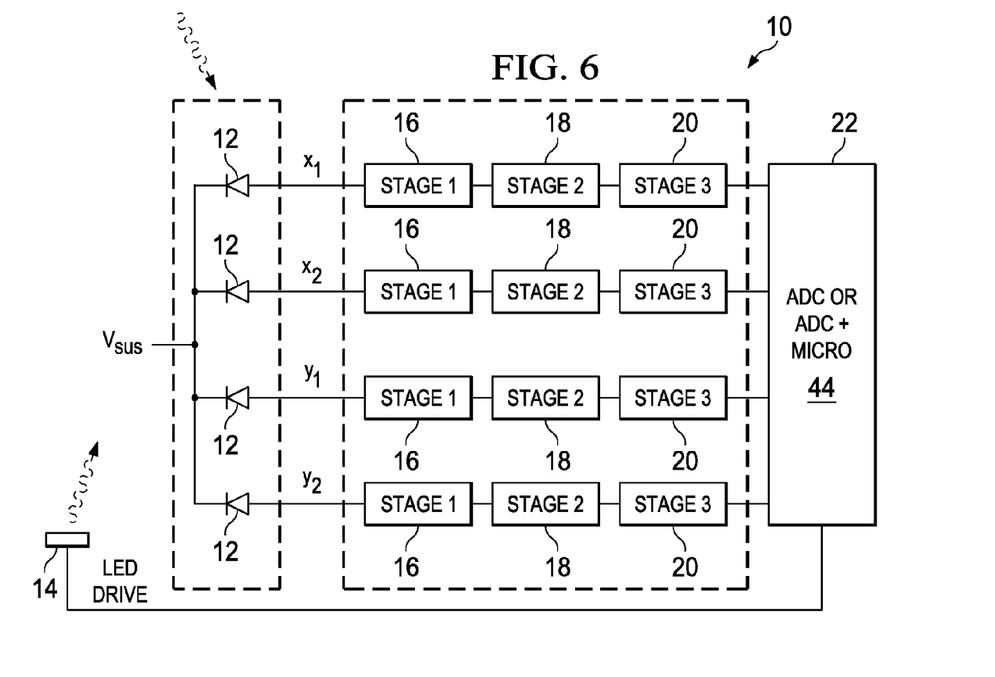
FIG. 6 is a simplified block diagram of another embodiment of the circuit architecture.

Turning to FIG. 6, FIG. 6 is a simplified block diagram illustrating another embodiment of electrical circuit 10. Multiple (e.g., four) sensors 12, shown in FIG. 6 as photodiodes 12, may be connected to ADC 44, for example, to measure light intensity from four different spatial orientations. In some embodiments, each sensor 12 may be connected to separate stages 16, 18 and 20, with all sensors 12 sharing a common ADC 44. Each of stages 20 may provide a positive integrated value and a negative integrated value to ADC 44. ADC 44 may sample the outputs from a specific stage 20 before proceeding to the next stage 20, and so on, until it samples the outputs from substantially all stage 20 within a certain time interval. The time interval may be configured according to the power cycle of light source 14, such that ADC 44 completes sampling the outputs from all stage 20 before light source 14 powers down.

Moreover, the output from stage 20 can remain constant after the integration phase until reset, ADC 44 can be multiplexed to sample each of the outputs without compromising performance. Thus embodiments of electrical circuit 10 can allow a relatively lower cost low speed ADC with low frequency switching between channels can be used without compromising performance. Such circuit architecture can be used in specialized photodiode applications, for example, that use lateral photodiodes, quad detectors, or optical angle sensors. With the circuit architecture of embodiments of electrical circuit 19, pulse width of the input light and substantially all components of stages 16, 18, and 20 can be configured with nanosecond pulses without substantially affecting ADC 44's sample rate.

Figure 7:
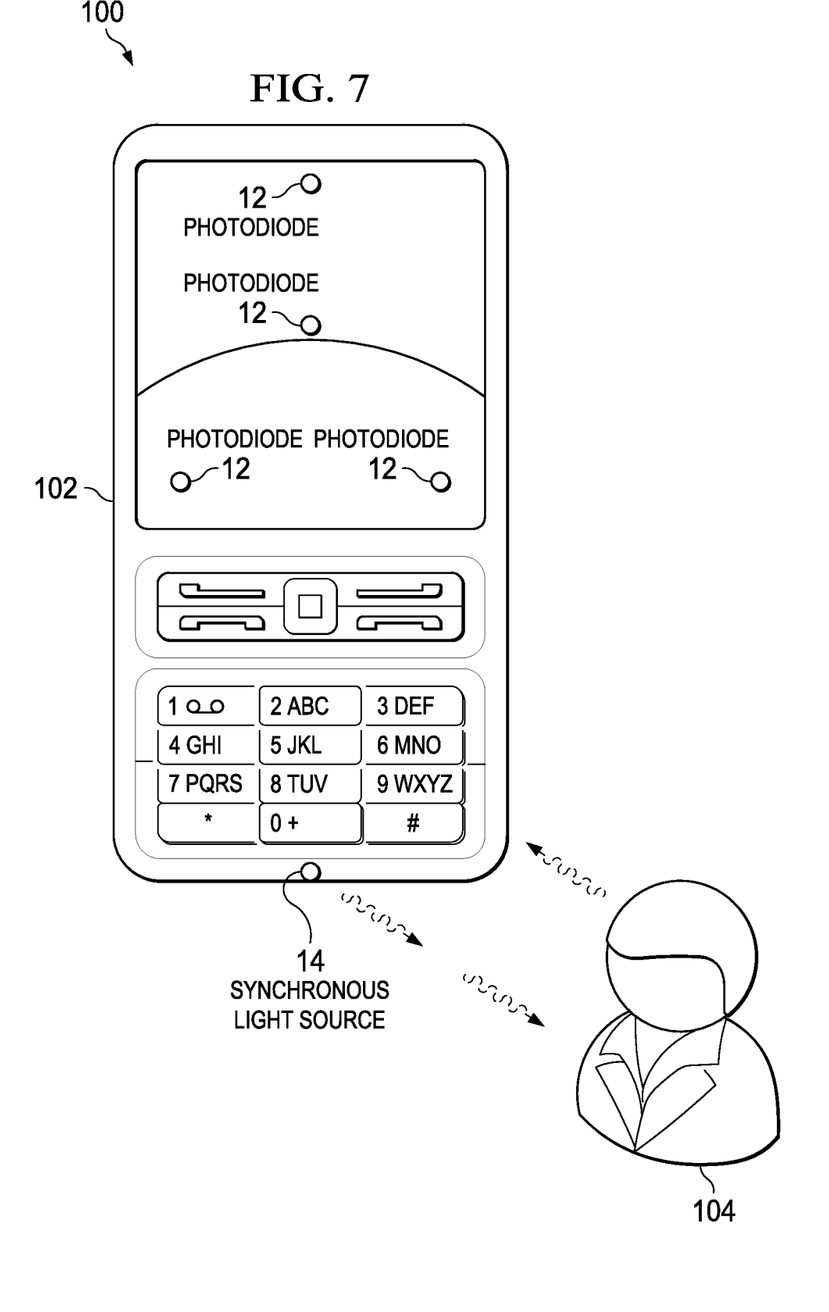
FIG. 7 is a simplified block diagram of example details of an application of an embodiment of the circuit architecture.

Turning to FIG. 7, FIG. 7 is a simplified diagram illustrating an example application 100 of electrical circuit 10. Smartphone 102 may be configured to detect gestures of a user 104 based on optical signals (rather than touch). Multiple photodiodes 12 may be configured on Smartphone 102 (e.g., on its display screen). Synchronous light source 14 may be provided on Smartphone 102 in some embodiments. Light from light source 14 may be reflected off user 104, and may be measured by photodiodes 12. The amount of light arriving at each photodiode 12 may depend on the particular gesture (hand, finger or body position) of user 104. When user 104 changes the gesture, the amount of light on photodiodes 12 may also change. This change may be calculated by a suitably calibrated microcontroller to detect the gesture and derive a suitable meaning thereof. With electrical circuit 10 implemented in such application 100, the sensitivity of the system to the background light and other extraneous light may be reduced without compromising the performance.

Figure 8:
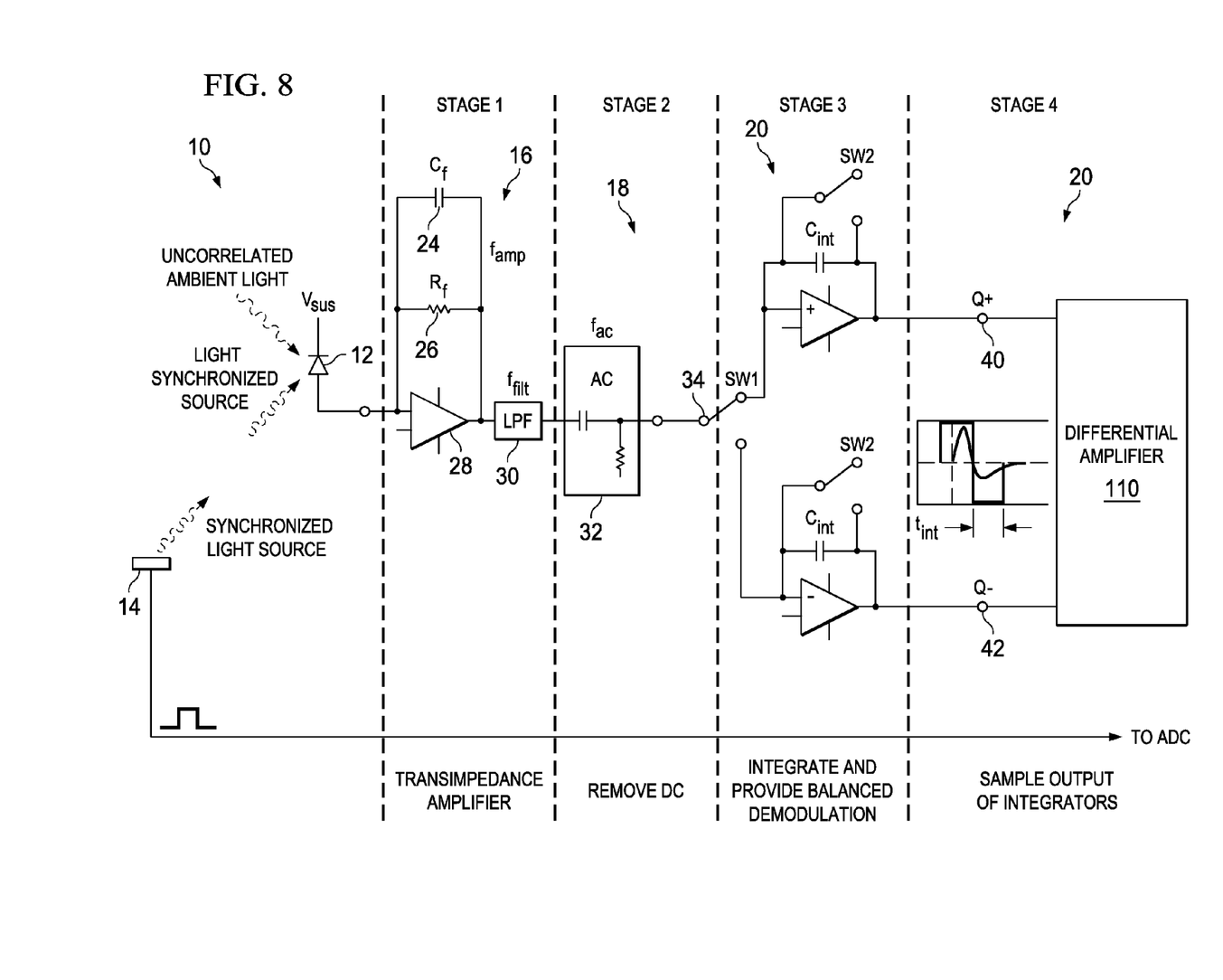
FIG. 8 is a simplified circuit diagram of another embodiment of the circuit architecture.

Turning to FIG. 8, FIG. 8 is a simplified circuit diagram illustrating another example configuration of an embodiment of electrical circuit 10. Instead of ADC 44, a differential amplifier 110 may be used in stage 22. Differential amplifier 110 may compute a difference between outputs 40 and 42 and send the difference to ADC 44 or other suitable component (e.g., microprocessor, digital signal processor, etc.). Differential amplifier 110 may also amplify the difference in outputs 40 and 42, and thereby increase accuracy of measurement based on particular needs.

For the example of sensor 12 being a photodiode, according to various implementations, the LED light can be any color. For example, a red or a green LED light may be used. Similarly, the LED pulse width can be any selected width, and in one example, the LED pulse width is about 3 µs. In other examples, the LED pulse width is less than about 3 µs, or more than about 3 µs. Pulse width of few ns to 100's of microsecond is a typical range for LED pulsewidths. The measurements can be repeated first as a burst of pulses, which are themselves repeated at various rates ranging from 0.01 Hz to many kHz.

In other embodiments when sensor 12 is a photodiode, the target light source could be any controllable light source, not necessarily a LED. Thus, target light sources could be, but are not limited to, e.g. laser diodes, high/low pressure gas discharge sources, inorganic/organic light emitting diodes, incandescent sources, halogen sources, etc.

VARIATIONS AND IMPLEMENTATIONS

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

In one example embodiment, electrical circuit 10 of the FIGURES may be implemented on a motherboard of an associated electronic device. The motherboard can be a general circuit board that can hold various components of the internal electronic system of the electronic device and, further, provide connectors for other peripherals. More specifically, the motherboard can provide the electrical connections by which the other components of the system can communicate electrically. Any suitable processors (inclusive of digital signal processors, microprocessors, supporting chipsets, etc.), memory elements, etc. can be suitably coupled to the motherboard based on particular configuration needs, processing demands, computer designs, etc. Other components such as external storage, additional sensors, controllers for audio/video display, and peripheral devices may be attached to the motherboard as plug-in cards, via cables, or integrated into the motherboard itself.

In another example embodiment, electrical circuit 10 of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the amplification functionalities may be implemented in one or more silicon cores in Application Specific Integrated Circuits (ASICs), Field Programmable Gate Arrays (FPGAs), and other semiconductor chips.

It is also imperative to note that all of the specifications, dimensions, and relationships outlined herein (e.g., the number of processors and memory elements, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that electrical circuit 10 of the FIGURES and its teachings are readily scalable and can accommodate a large number of components, as well as more complicated/sophisticated arrangements and configurations. Accordingly, the examples provided should not limit the scope or inhibit the broad teachings of electrical circuit 10 as potentially applied to a myriad of other architectures.

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Although the claims are presented in single dependency format in the style used before the USPTO, it should be understood that any claim can depend on and be combined with any preceding claim of the same type unless that is clearly technically infeasible.

What is claimed is:

1. A system, comprising:
   a sensor configured to generate a current signal, the current signal comprising at least a first portion comprising a contribution from a target source and/or a second portion comprising a contribution from one or more sources other than the target source;
   a first stage comprising an amplifier configured to amplify the current signal to generate a first stage output signal;
   a second stage comprising a filter configured to convert the first stage output signal to a second stage output signal having a positive amplitude, a negative amplitude, and a zero cross-over point between the positive amplitude and the negative amplitude;
   a third stage comprising:
      a positive integrating amplifier configured to receive the positive amplitude of the second stage output signal and generate a positive integrated value, and
      a negative integrating amplifier configured to receive the negative amplitude of the second stage output signal and generate a negative integrated value; and
   a fourth stage comprising at least an analog-to-digital converter (ADC) configured to generate one or more digital values indicative of the first portion of the current signal based on the positive and negative integrated values.

2. The system according to claim 1, wherein the amplifier includes an operational amplifier with a feedback loop comprising a feedback capacitor, a feedback resistor, and a low pass filter.

3. The system according to claim 2, where at least some components of one or more of the first stage, the second stage, the third stage, and the fourth stage are programmable.

4. The system according to claim 1, wherein the target source is a synchronous light source, a pulse of the synchronized light source has a duration of $\tau$, a bandwidth of the second stage is of the order of approximately $1/\tau$, and a corner frequency of the filter is set at $0.5/\tau$.

5. The system according to claim 1, wherein the second stage comprises an AC source and a capacitor.

6. The system according to claim 1, wherein the third stage comprises a switch configured to change from the positive integrating amplifier to the negative integrating amplifier at the occurrence of the zero cross-over point.

7. The system according to claim 6, wherein the switch is controlled by a timer.

8. The system according to claim 7, wherein the timer is configured to provide a clock synchronized with a frequency of the target source.

9. The system according to claim 1, wherein the ADC is configured to subtract the negative integrated value from the positive integrated value.

10. The system according to claim 1, wherein the fourth stage comprises a differential amplifier configured to subtract the negative integrated value from the positive integrated value.

11. The system according to claim 1, wherein the system is configured to substantially simultaneously provide sampling of multiple channels for analog-to-digital conversion.

12. The system according to claim 1, wherein the target source comprises a target light source, the sensor comprises a photodiode, and the current signal comprises a photocurrent signal, and wherein the system further comprises a photoplethysmography system connected thereto.

13. The system according to claim 12, wherein light from the light source is configured to be reflected of, or transmitted through an organ before reaching the photodiode.

14. The system according to claim 1, wherein the contribution to the current signal from the target source comprises a pulse or a series of repeating pulses.

15. The system according to claim 1, wherein the sensor comprises one or more of a capacitance sensor, an impedance sensor, a magnetic field sensor, and a piezo-electric film.

16. A system comprising:
    a plurality of sensors, wherein each sensor is configured to generate a current signal, the current signal comprising at least a first portion comprising a contribution from a respective target source and/or a second portion comprising a contribution from one or more sources other than the respective target source;
    a plurality of amplifiers, wherein each amplifier is configured to amplify the current signal from one of the sensors to generate a first stage output signal;
    a plurality of filters, wherein each filter is configured to convert the first stage output signal from each amplifier to a second stage output signal having a positive amplitude, a negative amplitude, and a zero cross-over point between the positive amplitude and the negative amplitude;
    a plurality of integrators, wherein at least one integrator comprises:
       a positive integrating amplifier configured to receive the positive amplitude of the second stage output signal from each filter and generate a positive integrated value, and
       a negative integrating amplifier configured to receive the negative amplitude of the second stage output signal from each filter and generate a negative integrated value; and
    an analog-to-digital converter (ADC) configured to process the positive and negative integrated values from the plurality of integrators.

17. The system according to claim 16, wherein the ADC comprises a low speed ADC having a total sampling time consistent with a power cycle of the target source.

18. The system according to claim 16, wherein the ADC comprises a high speed ADC configured to sample the outputs from each integrator at high frequency.

19. The system according to claim 16, wherein the system is coupled to a device configured to detect gestures of a user based on optical signals.

20. The system according to claim 16, wherein each sensor comprises one of a photodiode, a capacitance sensor, an impedance sensor, a magnetic field sensor, and a piezo-electric film.

* * * * *